US009952175B2

(12) United States Patent
Momose et al.

(10) Patent No.: US 9,952,175 B2
(45) Date of Patent: Apr. 24, 2018

(54) GAS SENSOR AND SENSOR DEVICE

(71) Applicant: FUJITSU LIMITED, Kawasaki-shi, Kanagawa (JP)

(72) Inventors: Satoru Momose, Atsugi (JP); Osamu Tsuboi, Kawasaki (JP); Ikuo Soga, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/353,028

(22) Filed: Nov. 16, 2016

(65) Prior Publication Data

US 2017/0067850 A1 Mar. 9, 2017

Related U.S. Application Data

(63) Continuation of application No. PCT/JP2014/065213, filed on Jun. 9, 2014.

(51) Int. Cl.
*H01L 29/02* (2006.01)
*G01N 27/414* (2006.01)
*G01N 27/416* (2006.01)
*C23C 14/16* (2006.01)
*C23C 14/58* (2006.01)
*H01L 29/16* (2006.01)
*H01L 29/20* (2006.01)
*H01L 29/24* (2006.01)
(Continued)

(52) U.S. Cl.
CPC ......... *G01N 27/4141* (2013.01); *C23C 14/16* (2013.01); *C23C 14/5846* (2013.01); *G01N 27/416* (2013.01); *H01L 29/16* (2013.01); *H01L 29/1608* (2013.01); *H01L 29/20* (2013.01); *H01L 29/2003* (2013.01); *H01L 29/242* (2013.01); *H01L 29/47* (2013.01); *G01N 33/0054* (2013.01)

(58) Field of Classification Search
CPC ............ G01N 27/4141; G01N 27/416; G01N 33/0054; C23C 14/5846; C23C 14/16; H01L 29/2003; H01L 29/242; H01L 29/1608; H01L 29/20; H01L 29/47; H01L 29/16
See application file for complete search history.

(56) References Cited

U.S. PATENT DOCUMENTS

| | | | | |
|---|---|---|---|---|
| 2007/0187699 A1* | 8/2007 | Sakata | ............ | C09K 11/565 257/79 |
| 2011/0124113 A1* | 5/2011 | Azad | .............. | G01N 27/125 436/139 |
| 2013/0234088 A1* | 9/2013 | Nishi | ............... | H01L 45/08 257/1 |

FOREIGN PATENT DOCUMENTS

| | | |
|---|---|---|
| JP | S63-238545 | 10/1988 |
| JP | H07-140100 | 6/1995 |

(Continued)

OTHER PUBLICATIONS

International Search Report for International Application No. PCT/JP2014/065213 dated Sep. 2, 2014.

(Continued)

*Primary Examiner* — Cuong B Nguyen
*Assistant Examiner* — Samuel Park
(74) *Attorney, Agent, or Firm* — Kratz, Quintos & Hanson, LLP

(57) ABSTRACT

A gas sensor including a first layer including copper (I) bromide, and a second layer, which is disposed on the first layer, and is a p-type semiconductor that is different from the copper (I) bromide, wherein one of the first layer and the second layer is more preferentially in contact with detection-target gas than the other.

9 Claims, 8 Drawing Sheets

(51) Int. Cl.
*H01L 29/47* (2006.01)
*G01N 33/00* (2006.01)

(56) References Cited

FOREIGN PATENT DOCUMENTS

| JP | 2002-031619 A1 | 1/2002 |
|---|---|---|
| JP | 2003-315299 A1 | 11/2003 |
| JP | 2005-221428 A1 | 8/2005 |
| JP | 2007-248335 A1 | 9/2007 |
| JP | 2008-145128 A1 | 6/2008 |
| JP | 2009-198346 A1 | 9/2009 |

OTHER PUBLICATIONS

P. Lauque, et al.; "Highly sensitive and selective room temperature NH3 gas microsensor using an ionic conductor (CuBr) film;" Analytica Chimica Acta; vol. 515; 2004; pp. 279-284 (6 Sheets)/Cited in International Search Report/p. 2 of specification.

P. Lauque, et al.; "Electrical properties and sensor characteristics for NH3 gas of sputtered CuBr films;" Sensors and Actuators B; vol. 59; 1999; pp. 216-219 (4 Sheets)/Cited in International Search Report.

M. Bendahan, et al.; "Development of an ammonia gas sensor;" Sensors and Actuators B; vol. 95; 2003; pp. 170-176 (7 Sheets)/Cited in International Search Report.

P. Lauque, et al.; "Electrical Properties of Thin-films of the Mixed Ionic-electronic Conductor CuBr: Influence of Electrode Metals and Gaseous Ammonia;" Journal of the European Ceramic Society; vol. 19; 1999; pp. 823-826 and front sheets (2), (6 Sheets total)/Cited in International Search Report.

B. Wolpert, et al.; "Chemosensitive properties of electrically conductive Cu(I) compounds at room temperature;" Sensors and Actuators B; vol. 134; 2008; pp. 839-842 (4 Sheets)/Cited in International Search Report.

* cited by examiner

GAS SENSOR AND SENSOR DEVICE

CROSS-REFERENCE TO RELATED APPLICATION

This application is a continuation application of International Application PCT/JP2014/065213 filed on Jun. 9, 2014 and designated the U.S., the entire contents of which are incorporated herein by reference.

FIELD

The embodiments discussed herein relate to a gas sensor, and a sensor device including the gas sensor.

BACKGROUND

As gas sensors detecting gas, such as ammonia, nitrogen oxide, and nitrogen monoxide, gas sensors that detect gas based on changes in electrical resistance have been conventionally used (for example, see Japanese Patent Application Laid-Open (JP-A) No. 07-140100). The gas sensors detect the gas based on changes in electrical resistance of a semiconductor due to adsorption of the gas on a surface of the semiconductor.

In the gas sensors that detect gas based on changes in electrical resistance, electric current needs to be supplied to the semiconductor using a constant-current power supply in order to measure changing electrical resistance. Therefore, the gas sensors that detect gas based on changes in electrical resistance have a problem that power consumption of a detection circuit itself becomes large.

Moreover, the semiconductor in the gas sensor needs to be heated to a temperature at which excellent detection properties can be obtained. Therefore, the gas sensor has a problem that a large quantity of power needs to be used for a heater configured to heat the gas sensor.

Accordingly, proposed are gas sensors, which detect gas based on changes in potential difference due to adsorption of the gas, not changes in electrical resistance. As such gas sensors, proposed are gas sensors, in each of which, for example, a porous silicon substrate and a single crystal silicon substrate are laminated, and gas sensors using solid electrolytes having ion conductivity, such as oxygen ion conductivity, oxide ion conductivity, and proton conductivity (for example, see JP-A Nos. 63-238545, 2002-031619, 2005-221428, 2007-248335, and 2009-198346).

However, the gas sensors using porous silicon substrates have a problem that it is difficult to produce the gas sensors on electronic parts, such as thin film transistors, because the porous silicon substrate is produced by anodizing a surface of a single crystal silicon substrate and the anodizing is a solution process.

In the gas sensors using solid electrolytes, moreover, temperatures, at which the solid electrolytes for use (e.g., zirconia) exhibit excellent ion conductivity, are high temperature of 300° C. or higher. In the proposed techniques, moreover, a chemical reaction, such as an oxidation reaction, of gas to be adsorbed is used for causing a change in a potential difference in the solid electrolyte, and therefore the gas sensor needs to be heated to a temperature at which the chemical reaction is induced. Accordingly, the proposed techniques have a problem that a large quantity of power needs to be used for a heater configured to heat the gas sensor.

Moreover, proposed as a gas sensor detecting gas at room temperature is a gas sensor, which is highly sensitive, is capable of highly selectively detecting $NH_3$ gas at room temperature, and uses a CuBr film (for example, see Pascal Lauque, Marc Bendahan, Jean-Luc Seguin, Kieu An Ngo, Philippe Knauth, Analytica Chimica Acta, 515, (2004), 279-284). In the proposed technique, gas is detected based on a change in electrical resistance. Accordingly, it is necessary to supply electric current to the CuBr film using a constant-current power supply in order to measure changes in electrical resistance, and there is a problem that power consumption of a detection circuit itself becomes large.

Accordingly, there is currently a need for a gas sensor that can be produced on electronic parts, does not require a supply of electric current using a constant-current power supply, does not need to be heated, and can be used with energy-saving efficiency, and a sensor device including such a gas sensor.

SUMMARY

According to the first aspect of the disclosed gas sensor, the disclosed gas sensor includes:
a first layer including copper (I) bromide; and
a second layer, which is disposed on the first layer, and is a p-type semiconductor that is different from the copper (I) bromide,
wherein one of the first layer and the second layer is more preferentially in contact with detection-target gas than the other.

The disclosed sensor device includes:
the disclosed gas sensor; and
a unit that is connected to the gas sensor and is configured to detect a change in potential difference of the gas sensor.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS (Gas Sensor)

Figure 1A:
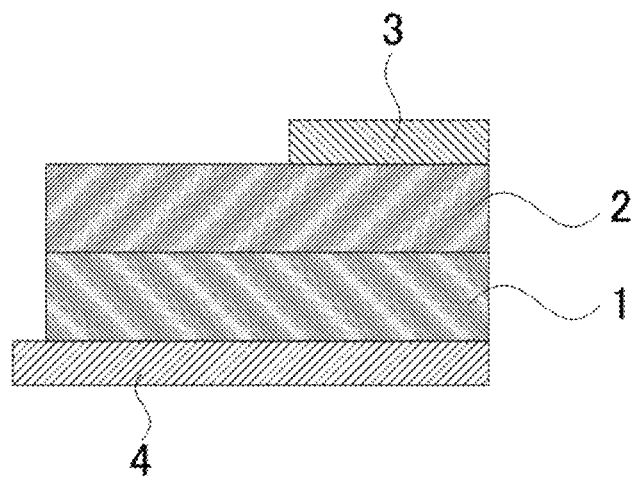
FIG. 1A is a schematic cross-sectional view illustrating one example of the first embodiment of the disclosed gas sensor.

The disclosed gas sensor include at least a first layer and a second layer, and may further include other members, such as an electrode, according to the necessity.

In the gas sensor, one of the first layer and the second layer is more preferentially in contact with detection-target gas than the other.

When the gas sensor is brought into contact with gas, spontaneous polarization is caused inside the gas sensor.

The phrase "more preferentially in contact with detection-target gas" means that an amount of electrons injected by the detection-target gas is relatively large. Examples of an embodiment of being more preferentially in contact with detection-target gas include an embodiment where an area on a surface of one of the first layer and the second layer in contact with the detection-target gas is larger than an area of a surface of the other layer in contact with the detection-target gas. Examples of such an embodiment include an embodiment where part of a surface of one of the first layer and the second layer is covered with an electrode but the rest of the surface is exposed, and an entire surface of the other layer is covered with an electrode.

The detection-target gas is not particularly limited, and may be appropriately selected depending on the intended purpose. Examples of the detection-target gas include nitrogen-containing compounds. Examples of the nitrogen-containing compounds include ammonia, amine, and nitrogen oxide.

One example of an embodiment of the disclosed gas sensor is described below.

First Embodiment

The first embodiment of the disclosed gas sensor is an embodiment where the second layer is more preferentially in contact with detection-target gas than the first layer.

<<First Layer>>

The first layer includes copper (I) bromide (CuBr). The first layer may be formed of the copper (I) bromide itself. Note that, the copper (I) bromide is a p-type semiconductor.

A size of the first layer is not particularly limited, and may be appropriately selected depending on the intended purpose.

<<Second Layer>>

The second layer is a p-type semiconductor that is different from the copper (I) bromide.

The second layer is disposed on the first layer. Specifically, the first layer and the second layer are in contact with each other.

The p-type semiconductor of the second layer is not particularly limited, and may be appropriately selected depending on the intended purpose. The p-type semiconductor is preferably $Ag_2O$, $Cu_2S$, $Cu_2O$, Ge, InP, Si, GaAs, SiC, or GaN. The p-type semiconductor is more preferably a compound including copper or silver, and particularly preferably $Ag_2O$, $Cu_2S$, or $Cu_2O$.

In the first embodiment, work function of the p-type semiconductor in the second layer is smaller than work function of the copper (I) bromide.

Examples of a measuring method of the work function include ultraviolet photoelectron spectroscopy (UPS), X-ray photoelectron spectroscopy (XPS), and cyclic voltammetry.

In order to determine the work function, the first layer or second layer in the gas sensor may be directly measured, or a layer corresponding to the first layer or the second layer may be separately produced and the produced layer may be measured.

A difference between the work function of the p-type semiconductor and the work function of the copper (I) bromide is not particularly limited, and may be appropriately selected depending on the intended purpose. When the difference is significantly small, the gas sensor is easily influenced by thermal disturbance to lower resolution of a measurement, and sensitivity of the gas sensor is substantially reduced. Therefore, the significantly small difference is not preferable. In this sense, the difference is preferably 0.5 eV or greater.

Formation methods of the first layer and the second layer are not particularly limited, and may be appropriately selected depending on the intended purpose. For example, the first layer and the second layer may be formed at the same time. For example, copper oxide ($Cu_2O$) that is a second layer may be formed at the same time as when a copper (I) bromide film (first layer) is produced by dipping copper in a copper (II) bromide aqueous solution. In this case, an interface between the first layer and the second layer may not be clear.

As described above, an interface between the first layer and the second layer in the gas sensor may not be clear as long as one of the first layer and the second layer is more preferentially in contact with the detection-target gas than the other. The same can be said to embodiments other than the first embodiment.

<<Electrode>>

In the first embodiment, an electrode is preferably further disposed.

The electrode is disposed on the second layer. For example, the electrode is disposed on part of a surface of the second layer at the opposite side to the side of the first layer.

A material of the electrode is not particularly limited, and may be appropriately selected depending on the intended purpose. Examples of the material include gold, silver, and platinum.

A formation method of the electrode is not particularly limited, and may be appropriately selected depending on the intended purpose. Examples of the formation method include vacuum deposition and sputtering.

The second layer and the electrode preferably form Schottky barrier junction. The Schottky barrier junction formed with the second layer and the electrode can enhance sensitivity of the sensor.

The Schottky barrier junction means a junction exhibiting rectifying characteristics.

<<Second Electrode>>

In the first embodiment, a second electrode is preferably further disposed.

The second electrode is disposed on the first layer. For example, the second electrode may be disposed on part of or entire surface of the first layer at the opposite side to the side of the second layer.

A material of the second electrode is not particularly limited, and may be appropriately selected depending on the intended purpose. Examples of the material include gold, silver, and platinum.

A formation method of the second electrode is not particularly limited, and may be appropriately selected depending on the intended purpose. Examples of the formation method include vacuum deposition and sputtering.

The first layer and the second electrode preferably form Schottky barrier junction. The Schottky barrier junction formed with the first layer and the second electrode can enhance sensitivity of the sensor.

One example of the first embodiment of the gas sensor is described with reference to FIGS. 1A and 1B.

The gas sensor of FIG. 1A include a first layer 1, a second layer 2, an electrode 3, and a second electrode 4.

The first layer 1 and the second layer 2 are in contact with each other.

The electrode 3 is formed on part of a surface of the second layer 2 at the opposite side to the side of the first layer 1. The second electrode 4 is formed on the entire surface of the first layer 1 at the opposite side to the side of the second layer 2. The second layer 2 is more preferentially in contact with detection-gas than the first layer 1 owing to the above-described structure.

In the above-described example, the detection-target gas of the gas sensor is ammonia, the first layer 1 is formed of copper (I) bromide (CuBr, work function: 7.1 eV), the second layer 2 is formed of copper oxide ($Cu_2O$, work function: 4.8 eV), and the electrode 3 and the second electrode 4 are formed of gold (work function: 5.1 eV).

Figure 1B:
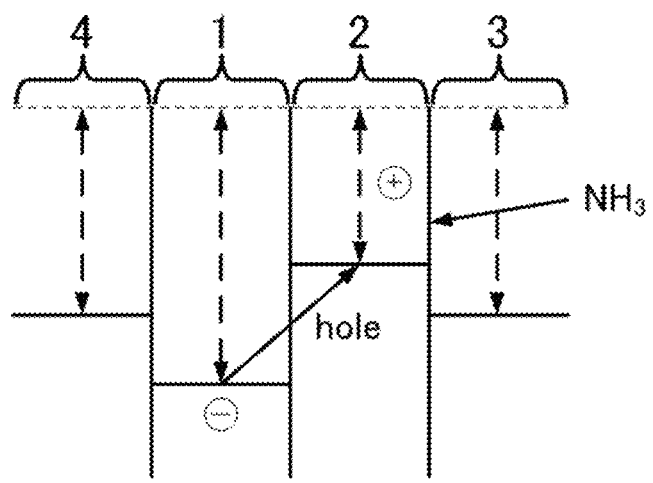
FIG. 1B is a schematic view illustrating a relationship of work function of the gas sensor of FIG. 1A.

The gas sensor of FIG. 1A has a relationship of the work function as illustrated in FIG. 1B. Note that, in FIG. 1B, a size of a broken-line arrow represents a size of the work function of the electrode or the semiconductor layer.

When ammonia is adsorbed on a surface of the second layer 2, the second layer 2 is doped with electrons from ammonia molecules having a reducing ability.

When the second layer 2 is negatively charged as a result of doping with electrons, holes are spontaneously moved from the first layer 1 having the larger work function to the second layer 2. However, the work function of the copper (I) bromide in the first layer 1 is larger than the work function of the gold in the second electrode 4 by about 2 eV, and thus the first layer 1 and the second electrode 4 form Schottky barrier junction. Therefore, it is difficult for the negative charge in the first layer 1 to flow out into the second electrode 4. As a result, the potential of the second electrode 4 connected to the first layer 1 becomes relatively lower than the potential of the electrode 3 connected to the first layer 1. Since electrons included in ammonia are supplied to un unoccupied orbital, when the ammonia is adsorbed on a surface of the second layer 2, the hole excess state is stabilized. As a result, the surface of the second layer 2, to which ammonia is adsorbed, is positively charged.

As described above, a change in the potential difference between the electrode 3 and the second layer 2 occurs, as result of adsorption of the detection-target gas onto the second layer 2.

An amount of electrons supplied to a semiconductor for doping from one ammonia molecule is determined depending on a semiconductor material to be a target, and an amount of the ammonia adsorbed on a surface of the semiconductor is proportional to an ammonia concentration in the atmosphere in the low concentration region. Accordingly, the generated potential different is almost proportional to the ammonia concentration in the atmosphere. Therefore, a concentration of the detection-target gas can be measured by measuring the potential difference between the electrode 3 and the second electrode 4 (a sensing electrode and a reference electrode).

Note that, ammonia and amine have a high ability of bonding, as a coordinate bond, to copper ions and silver ions of a compound including copper or silver, serving as a p-type semiconductor. Therefore, a gas sensor configured to selectively detect ammonia or amine can be obtained when the second layer 2 includes the compound including copper or silver as a p-type semiconductor.

Second Embodiment

The second embodiment of the disclosed gas sensor is an embodiment where the first layer is more preferentially in contact with detection-target gas than the second layer.
<<First Layer>>

The first layer include copper (I) bromide (CuBr). The first layer may be formed of the copper (I) bromide itself. Note that, the copper (I) bromide is a p-type semiconductor.

A size of the first layer is not particularly limited, and may be appropriately selected depending on the intended purpose.
<<Second Layer>>

The second layer is a p-type semiconductor that is different from the copper (I) bromide.

The second layer is disposed on the first layer. Specifically, the first layer and the second layer are in contact with each other.

The p-type semiconductor of the second layer is not particularly limited, and may be appropriately selected depending on the intended purpose. The p-type semiconductor is preferably $Ag_2O$, $Cu_2S$, $Cu_2O$, Ge, InP, Si, GaAs, SiC, or GaN.

In the second embodiment, the work function of the p-type semiconductor of the second layer is smaller than the work function of the copper (I) bromide.

A difference between the work function of the p-type semiconductor and the work function of the copper (I) bromide is not particularly limited, and may be appropriately selected depending on the intended purpose. When the difference is significantly small, the gas sensor is easily influenced by thermal disturbance to lower resolution of a measurement, and sensitivity of the gas sensor is substantially reduced. Therefore, the significantly small difference is not preferable. In this sense, the difference is preferably 0.5 eV or greater.
<<Electrode>>

In the second embodiment, the disclosed gas sensor include an electrode.

The electrode is disposed on the first layer. For example, the electrode is disposed on part of a surface of the first layer at the opposite side to the side of the second layer.

A material of the electrode is not particularly limited, and may be appropriately selected depending on the intended purpose. Examples of the material include gold, silver, and platinum.

A formation method of the electrode is not particularly limited, and may be appropriately selected depending on the intended purpose. Examples of the formation method include vacuum deposition and sputtering.

The first layer and the electrode preferably form Schottky barrier junction.

<<Second Electrode>>

In the second embodiment, a second electrode is preferably further disposed.

The second electrode is disposed on the second layer. For example, the second electrode may be disposed on part of or the entire surface of the second layer at the opposite side to the side of the first layer.

A material of the second electrode is not particularly limited, and may be appropriately selected depending on the intended purpose. Examples of the material include gold, silver, and platinum.

A formation method of the second electrode is not particularly limited, and may be appropriately selected depending on the intended purpose. Examples of the formation method include vacuum deposition and sputtering.

The second layer and the second electrode preferably form Schottky barrier junction.

One example of the second embodiment of the gas sensor is described with reference to FIGS. 2A and 2B.

Figure 2A:
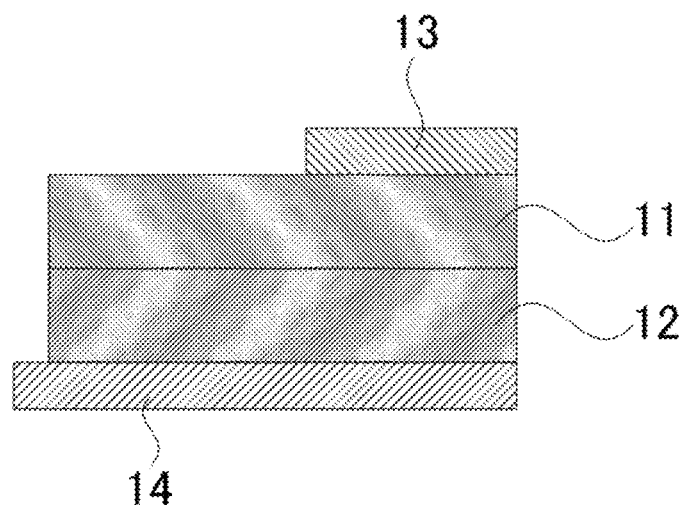
FIG. 2A is a schematic cross-sectional view illustrating one example of the second embodiment of the disclosed gas sensor.

The gas sensor of FIG. 2A includes a first layer 11, a second layer 12, an electrode 13, and a second electrode 14.

The first layer 11 and the second layer 12 are in contact with each other.

The electrode 13 is formed on part of a surface of the first layer 11 at the opposite side to the side of the second layer 12. The second electrode 14 is formed on the entire surface of the second layer 12 at the opposite side to the side of the first layer 11. The first layer 11 is more preferentially in contact with detection-target gas than the second layer 12 owing to the above-described structure.

In the above-described example, the detection-target gas of the gas sensor is ammonia, the first layer 11 is formed of copper (I) bromide (CuBr, work function: 7.1 eV), the second layer 12 is formed of a p-type silicon semiconductor (p-Si, work function: 5.1 eV), and the electrode 13 and the second electrode 14 are formed of gold (work function: 5.1 eV).

Figure 2B:
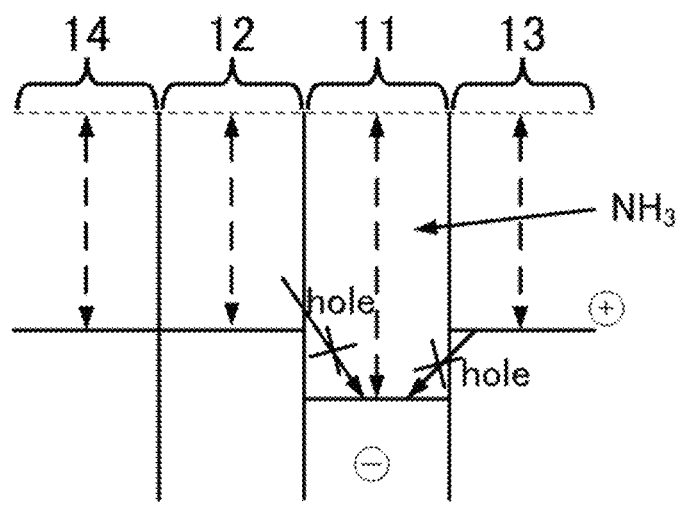
FIG. 2B is a schematic view illustrating a relationship of work function of the gas sensor of FIG. 2A.

The gas sensor of FIG. 2A has a relationship of the work function as illustrated in FIG. 2B. Note that, in FIG. 2B, a size of a broken-line arrow represents a size of the work function of the electrode or the layer.

When ammonia is adsorbed on a surface of the first layer 11, the first layer 11 is doped with electrons from ammonia molecules having a reducing ability. When the first layer 11 is negatively charged as a result of doping with electrons, the potential reduces. However, the work function of the gold in the electrode 13 is smaller than the work function of the copper (I) bromide in the first layer 11 by about 2 eV, and thus the first layer 11 and the electrode 13 form Schottky barrier junction. Therefore, it is difficult to inject holes into the first layer 11 from the electrode 13. Moreover, the work function of the p-type silicon semiconductor in the second layer 12 is smaller than the work function of the copper (I) bromide in the first layer 11 by about 2 eV. Therefore, it is also difficult to inject holes into the first layer 11 from the second layer 12. As a result, the negative charge in the first layer 11 is maintained, and a positive charge corresponded to the negative charge in the first layer is generated in the electrode 13 connected to the first layer 11. For example, in the case where the electrode 13 connected to the first layer 11 is used as a reference electrode, and the second electrode 14 connected to the second layer 12 is used as a sensing electrode, therefore, the gas sensor functions in the manner that the potential of the sensing electrode is lower than the potential of the reference electrode.

As described above, a change in the potential difference between the electrode 13 and the second electrode 14 occurs, as a result of adsorption of the detection-target gas onto the first layer 11.

An amount of electrons supplied to a semiconductor for doping from one ammonia molecule is determined depending on a semiconductor material to be a target, and an amount of the ammonia adsorbed on a surface of the semiconductor is proportional to an ammonia concentration in the atmosphere in the low concentration region. Accordingly, the generated potential different is almost proportional to the ammonia concentration in the atmosphere. Therefore, a concentration of the detection-target gas can be measured by measuring the potential difference between the electrode 13 and the second electrode 14 (a sensing electrode and a reference electrode).

As described above, the disclosed gas sensor utilizes doping of electrons to the p-type semiconductor from gas molecules, and polarization spontaneously occurs as a result of the carrier movement from the doping. Therefore, a highly sensitive gas sensor, which does not need to be heated, can be realized with a simple circuit of a low energy consumption.

Moreover, the disclosed gas sensor can be produced on electronic parts (e.g., field-effect transistors) because the gas sensor can be produced without a solution process, such as anodizing.

The disclosed gas sensor can solve the above-described various problems existing in the art, and can provide a gas sensor, which can be produced on a thin film transistor, does not require a supply of electric current using a constant-current power supply, does not need to be heated, and can be used with energy-saving efficiency.

(Sensor Device)

The disclosed sensor device includes at least the disclosed gas sensor and a unit configured to detect a change in potential difference of the gas sensor, and may further include other units according to the necessity.

<Unit Configured to Detect Change in Potential Difference of Gas Sensor>

The unit configured to detect a change in a potential difference of the gas sensor is not particularly limited, and may be appropriately selected depending on the intended purpose. The unit is preferably a field-effect transistor because the sensor device can be down sized, and the change in the potential difference can be amplified.

The unit configured to detect a change in a potential difference of the gas sensor is connected to an electrode included in the gas sensor.

<<Field-Effect Transistor>>

The field-effect transistor is not particularly limited, and may be appropriately selected depending on the intended purpose. Examples of the field-effect transistor include a field-effect transistor including a gate electrode configured to apply gate voltage, a source electrode and a drain electrode configured to take electric current out, an active layer arranged between the source electrode and the drain electrode, and a gate insulating layer arranged between the gate electrode and the active layer. Examples of a material of the active layer include silicon, and metal oxide semiconductors.

The electrode included in the gas sensor is connected to the gate electrode.

One example of the disclosed sensor device is described with reference to a drawing.

Figure 3:
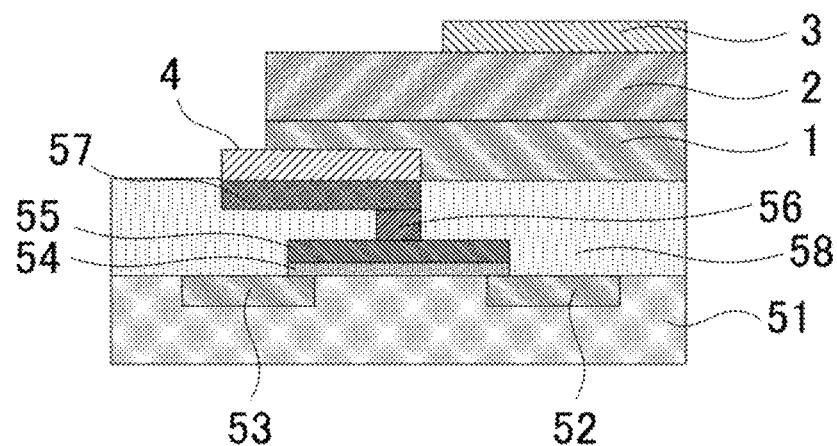
FIG. 3 is a schematic cross-sectional view illustrating one example of the disclosed sensor device.

FIG. 3 is a schematic cross-sectional view illustrating one example of the sensor device.

The sensor device illustrated in FIG. 3 includes a gas sensor and a field-effect transistor.

The gas sensor include a first layer 1, a second layer 2, an electrode 3, and a second electrode 4. The first layer 1 and the second layer 2 are in contact with each other. The electrode 3 is formed on part of a surface of the second layer 2 at the opposite side to the side of the first layer 1. The second electrode 4 is formed on part of a surface of the first layer 1 at the opposite side to the side of the second layer 2. An area not covered with the second electrode 4 on the surface of the first layer 1 at the opposite side to the side of the second layer 2 is covered with an insulating layer 58. Accordingly, the surface of the first layer 1 at the opposite side to the side of the second layer 2 is not brought into contact with the detection-target gas. Since the gas sensor has the above-described structure, the second layer 2 is more preferentially in contact with the detection-target gas than the first layer 1.

The field-effect transistor includes a silicon substrate 51 also functioning as an active layer, a source electrode 52, a drain electrode 53, a gate insulating layer 54, and a gate electrode 55. The source electrode 52 and the drain electrode 53 are arranged to sandwich the active layer. The gate insulating layer 54 is arranged between the active layer and the gate electrode 55. The second electrode 4 of the gas sensor and the gate electrode 55 of the field-effect transistor are connected to each other via a first line 56 and a second line 57. An insulating layer 58 is then formed to over the gate insulating layer 54, the gate electrode 55, the first line 56, and the second line 57, and the gas sensor is arranged on the insulating layer 58.

The disclosed sensor device can solve the above-described various problems existing in the art, and can provide a sensor device that does not need to be heated and can be used with energy-saving efficiency.

EXAMPLES

Examples of the present invention are explained below, but the present invention is not limited to the examples below in any way.

Example 1

Figure 4:
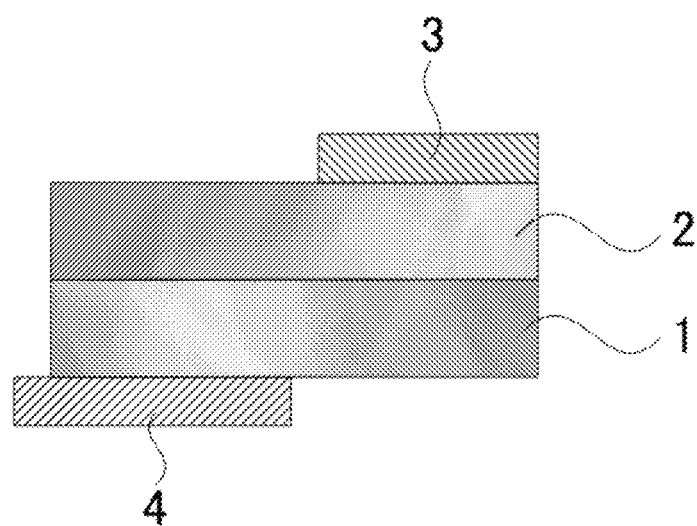
FIG. 4 is a schematic cross-sectional view of the gas sensor of Example 1.
Figure 5:
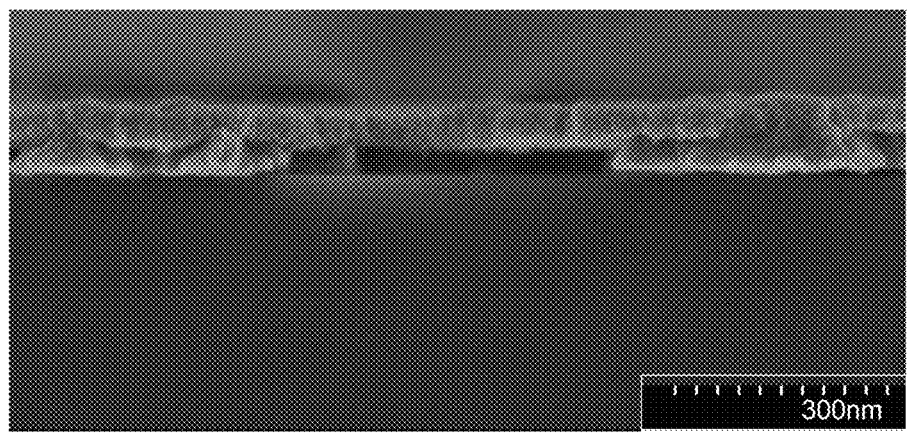
FIG. 5 is a SEM photograph of the copper film processed when the gas sensor of Example 1 was produced.
Figure 6:
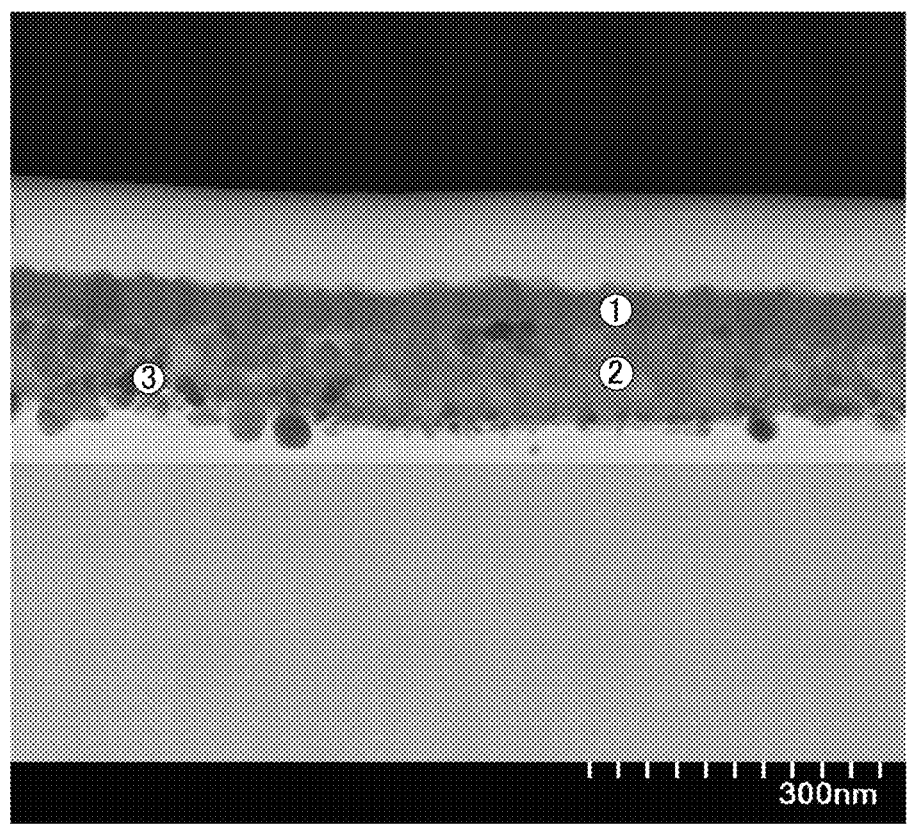
FIG. 6 is a STEM photograph of the copper film processed when the gas sensor of Example 1 was produced.
Figure 7A:
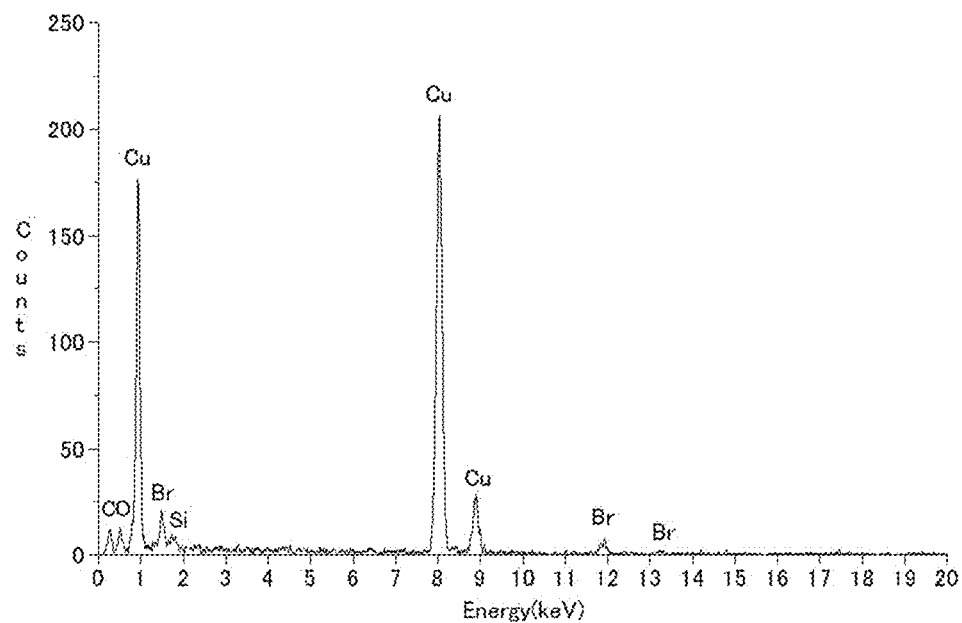
FIG. 7A depicts the EDX measurement result at the measuring point 1 of the copper film processed when the gas sensor of Example 1 was produced.
Figure 7B:
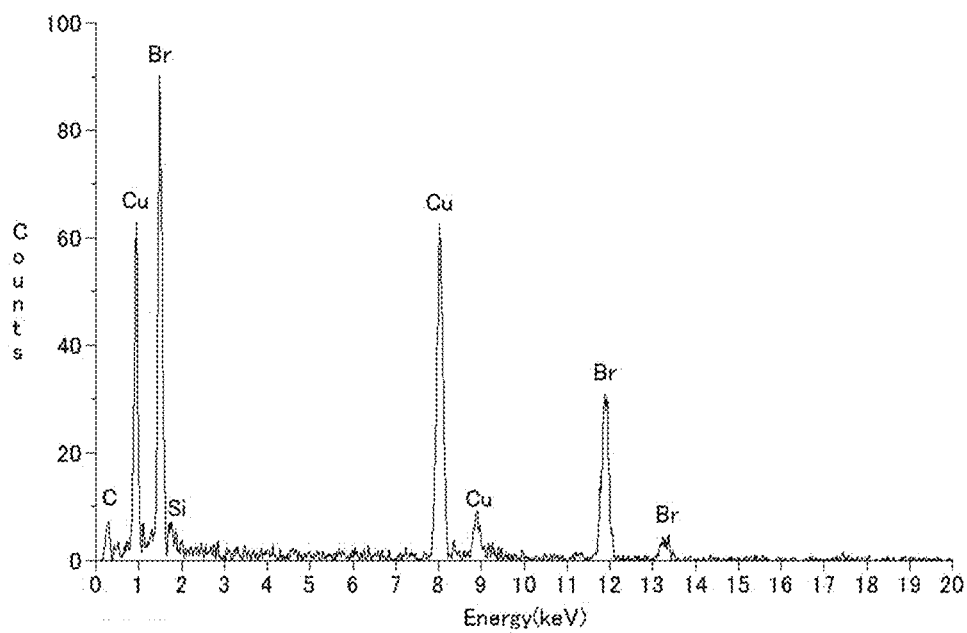
FIG. 7B depicts the EDX measurement result at the measuring point 2 of the copper film processed when the gas sensor of Example 1 was produced.
Figure 7C:
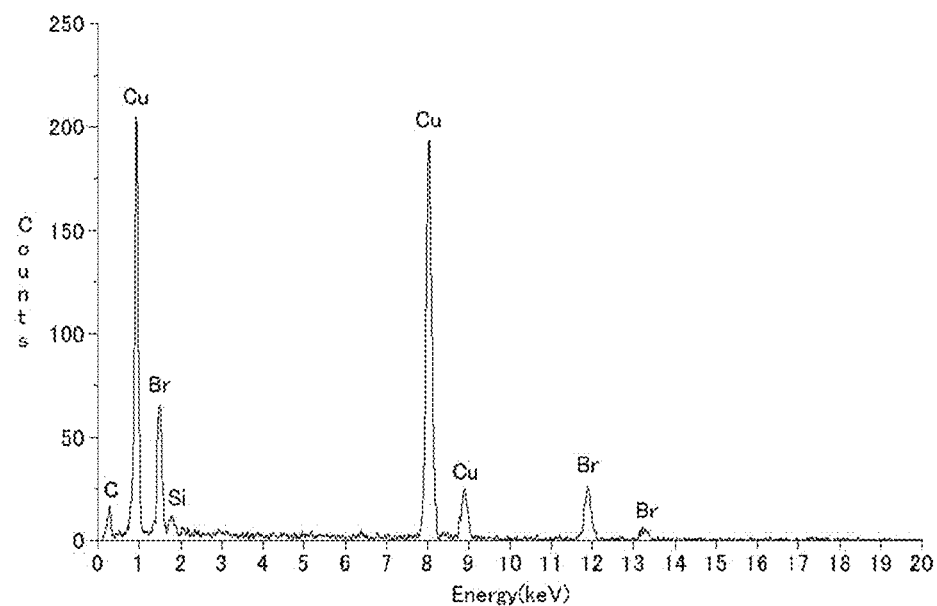
FIG. 7C depicts the EDX measurement result at the measuring point 3 of the copper film processed when the gas sensor of Example 1 was produced.
Figure 8:
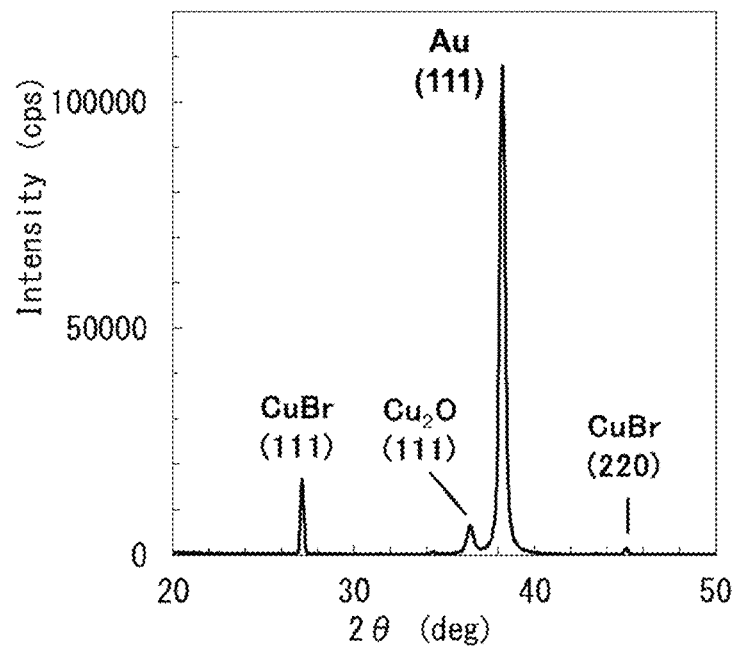
FIG. 8 depicts the XRD measurement result of the copper film processed when the gas sensor of Example 1 was produced.

A gas sensor as illustrated in FIG. 4 was produced. Specifically, the gas sensor was produced by the following method.
<Formation of Second Electrode>
A gold electrode (second electrode 4) having the width of 10 mm, the length of 20 mm, and the average thickness of 30 nm was formed by vacuum deposition on a silicon wafer having the length of 50 mm, the width of 10 mm, and the thickness of 0.63 mm, on a surface of which a thermally oxidized film having the average thickness of 1 μm had been formed.
<Formation of First Layer and Second Layer>
A copper film having the width of 8 mm, the length of 30 mm, and the average thickness of 60 nm was formed by vacuum deposition on the gold electrode. Subsequently, the copper film was dipped in a copper (II) bromide aqueous solution having a concentration of 1 mM for 30 minutes. As a result of this process, the copper film was turned into a film having the average thickness of 120 nm. The scanning electron microscope (SEM) image of the cross-section of the film obtained under the production conditions above is depicted in FIG. 5. The SEM image is taken at a position out of the gold electrode, and the two-layer structure depicted in the image is formed with the copper film. An elementary analysis was performed on the film by energy-dispersive X-ray spectroscopy (EDX). The scanning transmission electron microscope (STEM) image of the position on which the measurement was performed, and the measuring points of EDX (1, 2, and 3 in the order from the side of the surface) are depicted in FIG. 6. Moreover, the EDX measurement result at each measuring point is depicted in FIGS. 7A to 7C. Looking at the result from the bottom side, it can be confirmed that the measuring point "3" (FIG. 7C) is the state in the process of bromination, the measuring point "2" (FIG. 7B) is the state where the bromination is progressed, and the outermost surface (the measuring point "1") (FIG. 7A) is the state where oxygen is present replacing the reduction in the proportion of bromine. Moreover, the sample was subjected to X-ray diffraction (XRD) spectroscopy. The result is depicted in FIG. 8. Together with a diffraction line of the gold, which was the bottom electrode, the diffraction lines of CuBr and $Cu_2O$ were observed. Specifically, it was demonstrated that the film produced under the above-described conditions include the layer mainly including $Cu_2O$, which was a p-type semiconductor, at the upper part of the layer mainly including CuBr, which was a p-type semiconductor.

A laminate including a bottom electrode (gold electrode: second electrode 4), CuBr (first layer 1), and $Cu_2O$ (second layer 2) was formed by the same method to the above.
<Formation of Electrode>
Subsequently, a gold film having the width of 10 mm, the length of 20 mm, and the average thickness of 90 nm was formed as an upper electrode (electrode 3) by vacuum deposition in a manner that a length of a gap between the upper electrode and the bottom electrode was to be 1 mm. As a result, a gas sensor was produced.

Figure 9:
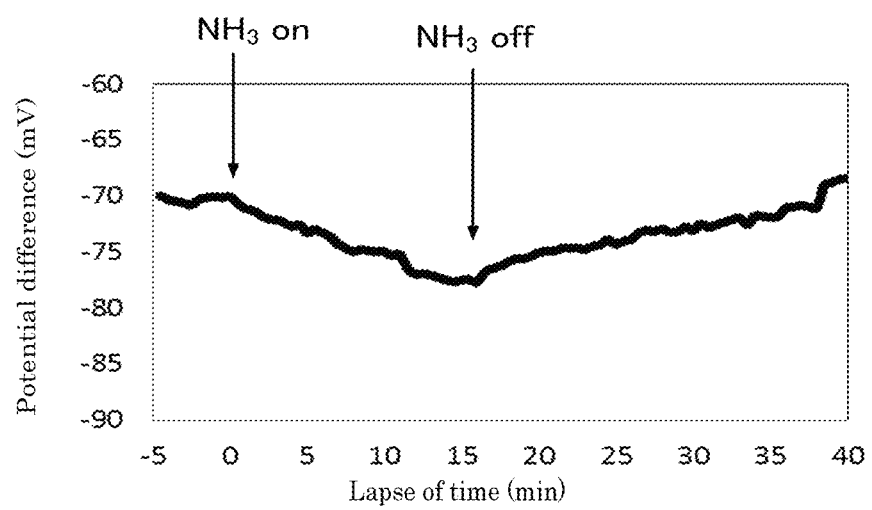
FIG. 9 is a graph depicting the measurement result of the potential difference of the gas sensor of Example 1.

The gap means a gap between the edge of the projected second electrode 4 and the edge of the electrode 3 facing each other, when the second electrode 4 is projected onto a plane of the second layer 2 to which the electrode 3 is disposed.
<Evaluation on Change in Potential Difference>
196 system DMM available from Keithley was connected to the produced gas sensor in a manner that the second electrode 4 was to be a sensing electrode and the electrode 3 was to be a reference electrode, and a potential difference between the both electrodes was measured. There was no difference in the potential between the both electrode of the gas sensor just after the production. After the aging process where the gas sensor was maintained in a nitrogen flow including ammonia at the concentration of 1 ppm at room temperature for 20 hours, the potential of the sensing electrode was lower than the reference electrode by about 70 mV. A response of the gas sensor to ammonia was evaluated by placing the gas sensor in a nitrogen gas flow path, and switching the gas source between nitrogen gas of high purity and nitrogen gas including ammonia at the concentration of 1 ppm. The response of the measured potential difference to ammonia and the lapse of time are presented in FIG. 9. When the air flow was switched from the nitrogen gas of high purity to the nitrogen gas including ammonia at the concentration of 1 ppm, the potential of the sensing electrode was further reduced, and the measured potential difference increased by about 7 mV. When the air flow was switched back to the nitrogen gas of high purity, the potential difference was recovered to the original state.

As described above, the gas sensor of high sensitivity and a potential difference measuring system was realized by forming a $Cu_2O$ layer (second layer), which was a p-type semiconductor having the smaller work function, on a surface of the copper (I) bromide (first layer), which was a p-type semiconductor, and measuring the potential difference between two electrodes connecting to the above-described two semiconductors.

Example 2

Figure 10:
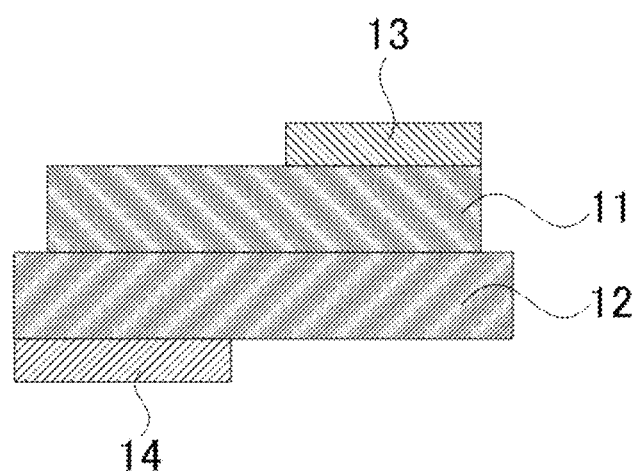
FIG. 10 is a schematic cross-sectional view of the gas sensor of Example 2.

A gas sensor as illustrated in FIG. 10 was produced. Specifically, the gas sensor was produced by the following method.

A CuBr film (first layer 11) having the length of 30 mm, the width of 8 mm, and the average thickness of 240 nm was formed by sputtering on a p-type silicon semiconductor (second layer 12) having the length of 50 mm, the width of 10 mm, and the average thickness of 0.6 mm. Gold electrodes (electrode 13 and second electrode 14) each having the side of 5 mm and the average thickness of 60 nm were formed respectively on a region where the p-type silicon semiconductor (second layer 12) was exposed, and on the CuBr film (first layer 11), to thereby obtain a gas sensor.

The potential difference between the both electrodes was measured in the same manner as in Example 1 by using the gold electrode (electrode 13) on the CuBr film (first layer 11) of the produced gas sensor as a reference electrode, and the gold electrode (second electrode 12) on the p-type silicon semiconductor (second layer 14) of the produced gas sensor as a sensing electrode. A response of the gas sensor to ammonia was evaluated by placing the gas sensor in a nitrogen gas flow path, and switching the gas source between nitrogen gas of high purity and nitrogen gas including ammonia at the concentration of 1 ppm.

Figure 11:
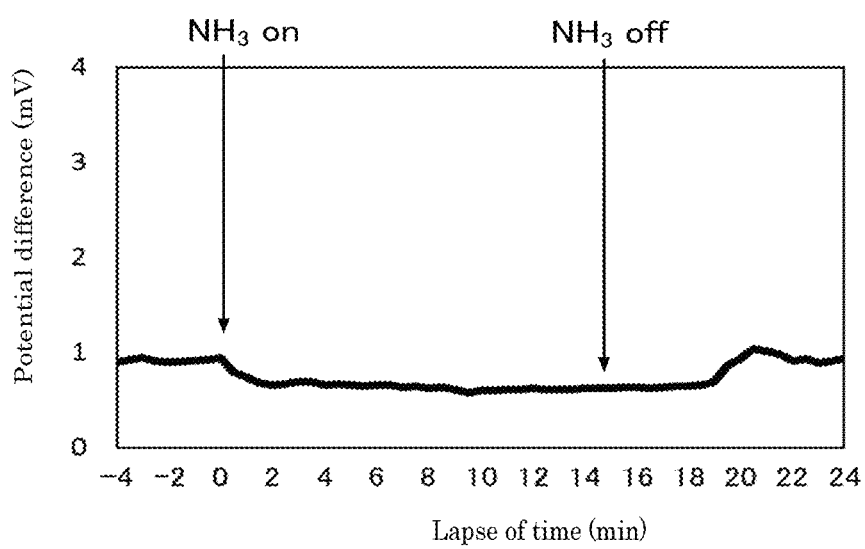
FIG. 11 is a graph depicting the measurement result of the potential difference of the gas sensor of Example 2.

The response of the measured potential difference to ammonia and the lapse of time are presented in FIG. 11. When the air flow was switched from the nitrogen gas of high purity to the nitrogen gas including ammonia at the concentration of 1 ppm, the potential of the sensing electrode was further reduced, and the measured potential difference increased by about 0.3 mV. When the air flow was switched back to the nitrogen gas of high purity, the potential of the sensing electrode was recovered to the original state.

As described above, the gas sensor of high sensitivity and a potential difference measuring system was realized by forming the layer formed of CuBr, which had the larger work function, and was a p-type semiconductor, on a surface of the p-type semiconductor, and forming the electrode connected to the CuBr using a material that formed the Schottky barrier with CuBr.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A gas sensor comprising:
   a first layer including copper (I) bromide; and
   a second layer, which is disposed on the first layer, and is a p-type semiconductor that is different from the copper (I) bromide,
   wherein work function of the p-type semiconductor is smaller than work function of the copper (I) bromide,
   wherein an area on a surface of the second layer in contact with detection-target gas is larger than an area of a surface of the first layer in contact with the detection-target gas, and
   wherein the first layer and the second electrode form a Schottky barrier junction.

2. A gas sensor comprising:
   a first layer including copper (I) bromide;
   a second layer, which is disposed on the first layer, and is a p-type semiconductor that is different from the copper (I) bromide; and
   an electrode disposed on the first layer,
   wherein the first layer and the electrode form a Schottky barrier junction,
   work function of the p-type semiconductor is smaller than work function of the copper (I) bromide, and
   wherein an area on a surface of the first layer in contact with detection-target gas is larger than an area of a surface of the second layer in contact with the detection-target gas.

3. The gas sensor according to claim 2, further comprising a second electrode disposed on the second layer,
   wherein the second layer and the second electrode form a Schottky barrier junction.

4. The gas sensor according to claim 1,
   wherein the p-type semiconductor is $Ag_2O$, $Cu_2S$, $Cu_2O$, Ge, InP, Si, GaAs, SiC, or GaN.

5. A sensor device comprising:
   the gas sensor according to claim 1; and
   a unit that is connected to the gas sensor and is configured to detect a change in potential difference of the gas sensor.

6. The sensor device according to claim 5,
   wherein the unit configured to detect a change in potential difference of the gas sensor is a field-effect transistor.

7. The gas sensor according to claim 2,
   wherein the p-type semiconductor is $Ag_2O$, $Cu_2S$, $Cu_2O$, Ge, InP, Si, GaAs, SiC, or GaN.

8. A sensor device comprising:
   the gas sensor according to claim 2; and
   a unit that is connected to the gas sensor and is configured to detect a change in potential difference of the gas sensor.

9. The sensor device according to claim 8,
   wherein the unit configured to detect a change in potential difference of the gas sensor is a field-effect transistor.

* * * * *